(12) United States Patent
Janssen et al.

(10) Patent No.: US 8,673,023 B2
(45) Date of Patent: *Mar. 18, 2014

(54) METHOD FOR PREPARING A COLORING COMPOSITION

(71) Applicant: Henkel AG & Co. KGaA, Duesseldorf (DE)

(72) Inventors: Frank Janssen, Neuss (DE); Juergen Schoepgens, Schwalmtal (DE); Armin Wadle, Erkrath (DE); Thomas Foerster, Duesseldorf (DE); Lisa Chen, Duesseldorf (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/652,219

(22) Filed: Oct. 15, 2012

(65) Prior Publication Data

US 2013/0036561 A1 Feb. 14, 2013

Related U.S. Application Data

(63) Continuation of application No. PCT/EP2010/065504, filed on Oct. 15, 2010.

(51) Int. Cl.
*A61Q 5/10* (2006.01)
(52) U.S. Cl.
USPC ............... 8/405; 8/406; 8/435; 8/109; 8/110; 8/111
(58) Field of Classification Search
USPC .................. 8/405, 406, 435, 109, 110, 111
See application file for complete search history.

(56) References Cited

U.S. PATENT DOCUMENTS

| 3,548,562 A | 12/1970 | Schwartzman |
| 4,635,822 A | 1/1987 | Klawitter |
| 5,061,289 A | 10/1991 | Clausen et al. |
| 2006/0002965 A1 | 1/2006 | Hoeffkes et al. |
| 2006/0164913 A1* | 7/2006 | Arramon ................ 366/139 |

FOREIGN PATENT DOCUMENTS

| DE | 1801518 A1 | 1/1971 |
| DE | 1617825 A1 | 1/1972 |
| DE | 2359399 A1 | 6/1975 |
| DE | 4133957 A1 | 4/1993 |
| DE | 4234887 A1 | 4/1994 |
| DE | 4440957 A1 | 5/1996 |
| DE | 19543988 A1 | 5/1997 |
| EP | 0132511 A2 | 2/1985 |
| EP | 0152761 A2 | 8/1985 |
| EP | 0998908 A1 | 5/2000 |
| EP | 998908 A2 | 5/2000 |
| EP | 2062616 A1 | 5/2009 |

OTHER PUBLICATIONS

European Patent Office, International Searching Authority, "International Search Report" mailed Oct. 26, 2012; International Appln. No. PCT/EP2010/065504, filed Oct. 15, 2010.

* cited by examiner

*Primary Examiner* — Eisa Elhilo
(74) *Attorney, Agent, or Firm* — Ingrassia Fisher & Lorenz, P.C.

(57) ABSTRACT

A method for manufacturing a coloring agent for keratin fibers from a first composition A and a second composition B is provided. The method comprises directing the first composition A from a container A by a filler apparatus through an inlet opening into a second container B containing the second composition B. In container B, as a result of the introduction of composition A and/or the action of the filler apparatus, at least one exit opening is formed out of which the coloring agent for keratin fibers exits from container B as a mixture of compositions A and B.

19 Claims, No Drawings

METHOD FOR PREPARING A COLORING COMPOSITION

CROSS-REFERENCE TO RELATED APPLICATION

This is a continuation of International Application No. PCT/EP2010/065504, filed Oct. 15, 2010, which was published under PCT Article 21(2) and which claims priority to German Application No. 10 2010 027 824.6, filed Apr. 15, 2010, which are all hereby incorporated in their entirety by reference.

TECHNICAL FIELD

The technical field relates to methods for preparing hair coloring compositions.

BACKGROUND

Human hair is treated today in many ways with cosmetic hair preparations. These include, for example, cleaning the hair with shampoos, care and regeneration using rinses and cures, and bleaching, coloring, and reshaping the hair using coloring agents, toning agents, waving agents, and styling preparations. Agents for modifying or tinting the color of head hair play a predominant role in this context.

For temporary coloring, it is usual to use coloring or toning agents that contain so-called substantive dyes as a coloring component. These are dye molecules that absorb directly onto the substrate and do not require an oxidizing process in order to form the color. Included among these dyes are, for example, henna, which has been known since antiquity for coloring the body and hair. These color results are, as a result, much more sensitive to shampooing than are the oxidation-based colors, so that a (very often undesirable) shift in tint, or even a visible loss of color, then occurs much more quickly.

So-called oxidizing coloring agents are used for permanent, intense coloring processes with corresponding fastness properties. Such coloring agents usually contain oxidation dye precursors, so-called developer components and coupler components. The developer components, under the influence of oxidizing agents or atmospheric oxygen, form among one another, or by coupling with one or more coupler components, the actual dyes. The oxidizing coloring agents are notable as a rule for outstanding, long-lasting color results. For natural-looking colors, it is usually necessary to use a mixture of a larger number of oxidation dye precursors; in many cases, substantive dyes are also used for toning.

These coloring agents, in particular oxidizing coloring agents or hair-bleaching powders, are as a rule manufactured by manually mixing prefabricated active-substance compositions, for example two oxidizing coloring agents. Manual intermixing is, however, time- and labor-intensive, since the constituents need, for example, to be weighed out before mixing. In addition, the user may be exposed to dust when processing solid active-substance compositions.

DETAILED DESCRIPTION

It has now been found that the aforementioned disadvantages of conventional mixing methods can be eliminated by a method for manufacturing a coloring agent for keratin fibers from a first composition A and a second composition B, in which method the first composition A is directed from container A
by means of a filler apparatus
through an inlet opening
into a second container B containing the second composition B, wherein composition A is introduced into container B, and container B forms, as a result of the introduction of composition A and/or the action of the filler apparatus, at least one exit opening out of which the coloring agent for the keratin fibers exits from container B as a mixture of compositions A and B.

In the context of the method herein, two compositions A and B differing from one another are mixed with one another to constitute a coloring agent for keratin fibers.

Composition A is introduced from a container A. This container A is configured in an embodiment as a storage container, and for example encompasses several times the amount of composition A needed for carrying out a single mixing method. In other words, in an exemplary embodiment of the method, a sub-quantity a of composition A present in container A is introduced into container B, a residual quantity of composition A present in container A remaining in container A until the end of the mixing method, and that residual quantity corresponding to twice, for example four times, such as at least eight times the quantity of sub-quantity a.

In a further embodiment, container A comprises two or more chambers (e.g., A1 and A2) in which compositions (e.g., A1 and A2) differing from one another are present separately from one another. The apparatus used to carry out the method herein is embodied in such a way that the user selects between the two or more chambers and alternatively uses, for example, a composition A1 in a first mixing method and a composition A2 in the subsequent mixing method.

Alternatively to the above-described multi-chamber configuration of container A, the apparatus for carrying out the method herein can also provide two or more separate containers for the reception of different compositions A.

The introduction of composition A from container A into container B is accomplished by means of a directing system attaching to container A. Located at the end of this directing system is the filler apparatus provided for introducing composition A into container B. To shorten the duration of the method and to improve the method's results, in particular the intermixing quality, composition A is introduced into container B for example at a pressure above about 1.1 bar, for example above about 2.0 bar, for example above about 5.0 bar, such as in the range of from about 10 to about 20 bar.

Composition A is introduced in the course of the method into container B, out of which the coloring agent for keratin fibers then exits from container B as a mixture of compositions A and B.

Container B used for this is fastened, for example by means of an adhesive, latching, snap-on, or clamping mechanism, in the apparatus used to carry out the method.

In an embodiment, container B is embodied in the form of a sealed capsule. In one embodiment of the method, this sealed capsule is opened by means of the directing system conveying composition A. The opening operation occurs for example by penetration of the container wall of container B, for example by means of the filler apparatus located at the end of the directing system. This filler apparatus can be embodied, for example, in the form of a spike. Once the container wall has been punched through, composition A is then introduced into container B.

In an embodiment of the method, at least one exit opening is formed in container B as a result of the introduction of composition A. The reason for the formation of the exit opening can be, for example, the increasing pressure in container B. Alternatively, however, the exit opening can also be formed by the action of the filler apparatus, for example by the fact that the filler apparatus pushes through the container wall of container B at two points, or by the fact that the pressure occurring in the container as a result of penetration of a container wall causes formation of the exit opening.

The formation of the exit opening in the container wall of container B, in particular the exact location at which the exit opening is formed, is controlled by the specific construction of container B.

In a first embodiment, container B possesses a weakening line along which the exit opening is formed as a result of the introduction of composition A and/or the action of the filler apparatus.

In another embodiment, the container possesses a membrane that is pressed against a spike, accompanied by formation of the exit opening, as a result of the introduction of composition A and/or the action of the filler apparatus. The membrane is by example a constituent of the container wall of container B. The exit opening is generated by the penetration of the membrane by the spike. The spike can be arranged both inside container B, and outside container B. In the case of a spike arranged inside container B. the container wall of container B is opened from the inside outward. If the spike is located outside container B, the spike pushes the container wall from the outside inward. The container wall of container B comprises, in the area of action of the spike, a weakening line by which, for example, the size of the exit opening can be influenced.

To improve the mixing effect, composition A and/or the mixture of compositions A and B preferably passes through a static mixer in the course of the method. This static mixer can be arranged, for example, inside the above-described directing system, but is preferably located in the immediate vicinity of the exit opening of container B, for example inside container B or outside the exit opening. In the latter case the static mixer can be embodied as an integral constituent of container B. Alternatively, the static mixer is a constituent of the apparatus used to carry out the method contemplated herein, and is associated, for example, with the adhesive, latching, snap-on, or clamping mechanism used to fasten container B.

Composition B present in container B is discharged in the course of the method, by means of the introduced composition A, out of container B through the exit opening. Discharge occurs, for example, substantially completely. In other words, at least about 80 wt. %, for example at least about 90 wt. %, for example at least about 95 wt. %, such as at least about 98 wt. % of composition B is discharged from the container.

The volume ratio of compositions A and B used in the mixing method is for example from about 10:1 to about 1:1, such as about 6:1 to about 2:1. The absolute volume of composition A used is, for example, in the range of from about 5 to about 500 ml, for example in the range of from about 10 to about 400 ml, such as in the range of from about 20 to about 300 ml.

In an exemplary embodiment, compositions A and B are not heated by an external heat source in the course of the mixing method. The temperature of composition A should be for example less than about 35° C., for example less than about 30° C., such as less than about 25° C. The temperature of the coloring agent for keratin fibers upon exiting from container B should likewise be for example less than about 35° C., for example less than about 30° C., such as less than about 25° C.

Compositions A and B that are mixed with one another in the method contemplated herein can contain a plurality of hair-color-changing active substances. For example, two different oxidizing coloring agents, two different toning agents, two different strong hair-bleaching agents, a hair-bleaching agent and an oxidizing coloring agent, a hair-bleaching agent and a toning agent, or an oxidizing agent and a toning agent can be mixed in the method contemplated herein to yield a coloring agent for keratin fibers.

Composition A is, for example, flowable and is present in the form of a liquid, a gel, or a paste. Exemplary liquid compositions A contain at least about 30 wt. %, for example at least about 40 wt. %, such as at least about 50 wt. % water. The weight proportion of water is for example in the range of from about 30 to about 98 wt. %, for example in the range of from about 40 to about 96 wt. %, such as in the range of from about 50 to about 94%, based in each case on the total weight of composition A.

In an exemplary embodiment of the method, composition A contains at least one oxidizing agent, for example about 0.5 to about 50 wt. %, for example about 1.0 to about 20 wt. %, for example about 2.5 to about 16 wt. %, such as about 5.0 to about 14 wt. % hydrogen peroxide (calculated as 100% $H_2O_2$), based in each case on the total weight of composition A.

To adjust the viscosity, composition A can contain a thickening agent, for example, about 1.0 to about 30 wt. %, for example about 3.0 to about 25 wt. %, such as about 5.0 to about 20 wt. % of at least one homo- or copolymer that is constituted from a monomer mixture of ethylenically unsaturated acids and/or simple $C_1$ to $C_6$ alkyl esters thereof, based in each case on the total weight of composition A, are used.

Composition B can be present in flowable form, for example as a liquid, gel, or paste, but also as a solid, in particular as a powder or compressed powder. In terms of the duration of the method and in order to improve the method's results, in particular the mixing quality, however, flowable compositions B have proven to solid ones.

The method contemplated herein serves for simple and efficient manufacture of coloring agents for keratinic fibers. Corresponding agents therefore of course contain suitable coloring or decolorizing active substances. Exemplary variants of the method are characterized in that composition B contains at least one oxidation dye precursor or at least one substantive dye.

In an exemplary embodiment, composition B contains at least one oxidizing coloring agent (oxidation dye precursor).

"Oxidizing coloring agents" are to be understood as used herein as hair-color-changing agents that produce a permanent coloration of the fibers by means of the oxidation of oxidation dye precursors.

The exemplary embodiments of the method herein are subject to no restrictions whatsoever with regard to the dye precursors usable in compositions B. Compositions B can contain, as dye precursors, oxidation dye precursors of the developer and/or coupler type, and precursors of bioanalogous dyes such as indole and indoline derivatives, as well as mixtures of representatives of these groups.

In exemplary embodiment, compositions B contains at least one oxidation dye precursor of the developer and/or coupler type.

A developer component a p-phenylenediamine derivative or a physiologically acceptable salt thereof may be used. Particularly suitable are p-phenylenediamine derivatives of formula (E1)

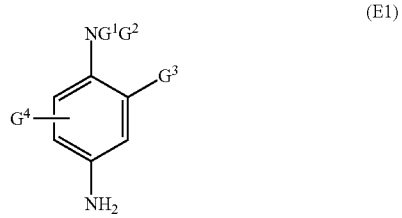

where
- $G^1$ denotes a hydrogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$) alkoxy-($C_1$ to $C_4$)alkyl residue, a 4'-aminophenyl residue, or a $C_1$ to $C_4$ alkyl residue that is substituted with a nitrogen-containing group, with a phenyl residue, or with a 4'-aminophenyl residue;
- $G^2$ denotes a hydrogen atom, a $C_1$ to $C_4$ alkyl residue, $C_1$ to $C_4$ monohydroxyalkyl residue, a $C_2$ to $C_4$ polyhydroxyalkyl residue, a ($C_1$ to $C_4$) alkoxy-($C_1$ to $C_4$)alkyl residue or a $C_1$ to $C_4$ alkyl residue that is substituted with a nitrogen-containing group;
- $G^3$ denotes a hydrogen atom, a halogen atom such as a chlorine, bromine, iodine, or fluorine atom, a $C_1$ to $C_4$ alkyl residue, a $C_1$ to $C_4$ monohydroxyalkyl residue, a $C_2$ to $C_4$ polyhydroxyalkyl residue, a $C_1$ to $C_4$ hydroxyalkoxy residue, a $C_1$ to $C_4$ acetylaminoalkoxy residue, a $C_1$ to $C_4$ mesylaminoalkoxy residue, or a $C_1$ to $C_4$ carbamoylaminoalkoxy residue;
- $G^4$ denotes a hydrogen atom, a halogen atom, or a $C_1$ to $C_4$ alkyl residue; or
- if $G^3$ are $G^4$ are in the ortho-position with respect to one another, they can together form a bridging $\alpha,\omega$-alkylenedioxo group, for example an ethylenedioxy group.

Examples of the $C_1$ to $C_4$ alkyl residues recited as substituents in the compounds herein are the methyl, ethyl, propyl, isopropyl and butyl groups. Ethyl and methyl are exemplary alkyl residues. $C_1$ to $C_4$ alkoxy residues suitable for use herein are, for example, a methoxy or an ethoxy group. A hydroxymethyl, 2-hydroxyethyl, 3-hydroxypropyl, or 4-hydroxybutyl group may also be recited as suitable examples of a $C_1$ to $C_4$ hydroxyalkyl group. A 2-hydroxyethyl group is particularly suitable. A particularly suitable $C_2$ to $C_4$ polyhydroxyalkyl group is the 1,2-dihydroxyethyl group. Examples of halogen atoms are F, Cl, or Br atoms; Cl atoms are particularly suitable. The additional terms used are derived from the definitions given here. Examples of nitrogen-containing groups of formula (E1) are, in particular, the amino groups, $C_1$ to $C_4$ monoalkylamino groups, $C_1$ to $C_4$ dialkylamino groups, $C_1$ to $C_4$ trialkylammonium groups, $C_1$ to $C_4$ monohydroxyalkylamino groups, imidazolinium, and ammonium.

Particularly preferred p-phenylenediamines of formula (E1) are selected from p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-($\beta$-hydroxyethyl)-p-phenylenediamine, 4-N,N-bis-($\beta$-hydroxyethyl)amino-2-methylaniline, 4-N,N-bis-($\beta$-hydroxyethyl) amino-2-chloroaniline, 2-($\beta$-hydroxyethyl)-p-phenylenediamine, 2-($\alpha,\beta$-dihydroxyethyl)-p-phenylenediamine, 2-fluoro-p-phenylenediamine, 2-isopropyl-p-phenylenediamine, N-($\beta$-hydroxypropyl)-p-phenylenediamine, 2-hydroxymethyl-p-phenylenediamine, N,N-dimethyl-3-methyl-p-phenylenediamine, N,N-(ethyl,$\beta$-hydroxyethyl)-p-phenylenediamine, N-($\beta,\gamma$-dihydroxypropyl)-p-phenylenediamine, N-(4'-aminophenyl)-p-phenylenediamine, N-phenyl-p-phenylenediamine, 2-($\beta$-hydroxyethyloxy)-p-phenylenediamine, 2-($\beta$-acetylaminoethyloxy)-p-phenylenediamine, N-($\beta$-methoxyethyl)-p-phenylenediamine, N-(4-amino-3-methylphenyl)-N-[3-(1H-imidazole-1-yl)propyl]amine, and 5,8-diaminobenzo-1,4-dioxane, as well as physiologically acceptable salts thereof.

Exemplary p-Phenylenediamine derivatives of formula (E1) are p-phenylenediamine, p-toluoylenediamine, 2-($\beta$-hydroxyethyl)-p-phenylenediamine, 2-($\alpha,\beta$-dihydroxyethyl)-p-phenylenediamine, and N,N-bis-($\beta$-hydroxyethyl)-p-phenylenediamine.

It may furthermore be suitable to use as developer components compounds that contain at least two aromatic nuclei that are substituted with amino and/or hydroxyl groups.

Among the binuclear developer components that can be used in the coloring compositions may be cited, in particular, those compounds that correspond to formula (E2) below, as well as physiologically acceptable salts thereof:

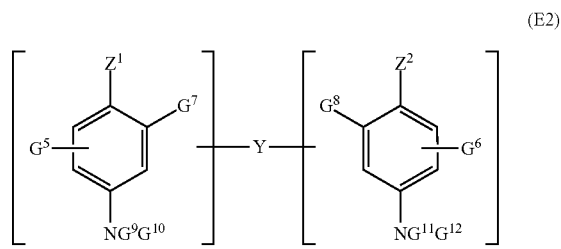

where:
- $Z^1$ and $Z^2$ denote, mutually independently, a hydroxyl or $NH_2$ residue that is optionally substituted with a $C_1$ to $C_4$ alkyl residue, with a $C_1$ to $C_4$ hydroxyalkyl residue, and/or with a bridge Y, or that optionally is part of a bridging ring system;
- bridge Y denotes an alkylene group having 1 to 14 carbon atoms, for example a linear or branched alkylene chain or an alkylene ring, which can be interrupted or terminated by one or more nitrogen-containing groups and/or one or more heteroatoms such as oxygen, sulfur, or nitrogen atoms, and possibly can be substituted with one or more hydroxyl or $C_1$ to $C_8$ alkoxy residues, or a direct bond;
- $G^5$ and $G^6$ denote, mutually independently, a hydrogen or halogen atom, a $C_1$ to $C_4$ alkyl residue, a $C_1$ to $C_4$ monohydroxyalkyl residue, a $C_2$ to $C_4$ polyhydroxyalkyl residue, a $C_1$ to $C_4$ aminoalkyl residue, or a direct bond to bridge Y,
- $G^7$, $G^8$, $G^9$, $G^{10}$, $G^{11}$ and $G^{12}$ denote, mutually independently, a hydrogen atom, a direct bond to bridge Y, or a $C_1$ to $C_4$ alkyl residue, with the provision that the compounds of formula (E2) contain only one bridge Y per molecule.

The substituents used in formula (E2) are defined herein by analogy with the statements made above.

Exemplary binuclear developer components of formula (E2) are, in particular: N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)ethylenediamine, N,N'-bis-(4-aminophenyl)tetramethylenediamine, N,N'-bis-(β-hydroxyethyl)-N,N'-bis-(4-aminophenyl)tetramethylenediamine, N,N'-bis-(4-methylaminophenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine, and 1,10-bis-(2',5'-diaminophenyl)-1,4,7,10-tetraoxadecane, and physiologically acceptable salts thereof.

Further exemplary binuclear developer components of formula (E2) are N,N'-bis-(β-hydroxyethyl)-N,N'-bis-(4'-aminophenyl)-1,3-diaminopropan-2-ol, bis-(2-hydroxy-5-aminophenyl)methane, 1,3-bis-(2-hydroxy-5-aminophenyl)methane, N,N'-bis-(4'-aminophenyl)-1,4-diazacycloheptane, and 1,10-bis-(2',5'-diaminophenyl)-1,4,7,10-tetraoxadecane, or a physiologically acceptable salt thereof.

It may furthermore be suitable to use as a developer component a p-aminophenol derivative or one of its physiologically acceptable salts. p-Aminophenol derivatives of formula (E3) are particularly suitable:

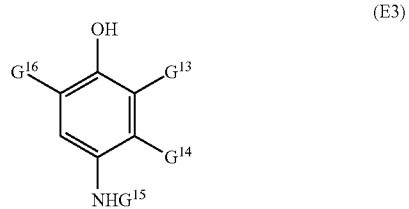

(E3)

where:
G$^{13}$ denotes a hydrogen atom, a halogen atom, a C$_1$ to C$_4$ alkyl residue, a C$_1$ to C$_4$ monohydroxyalkyl residue, a C$_2$ to C$_4$ polyhydroxyalkyl residue, a (C$_1$ to C$_4$)alkoxy-(C$_1$ to C$_4$)alkyl residue, a C$_1$ to C$_4$ aminoalkyl residue, a hydroxy-(C$_1$ to C$_4$)alkylamino residue, a C$_1$ to C$_4$ hydroxyalkoxy residue, a C$_1$ to C$_4$ hydroxyalkyl-(C$_1$ to C$_4$)aminoalkyl residue, or a (di-C$_1$ to C$_4$ alkylamino)-(C$_1$ to C$_4$)alkyl residue, and G$^{14}$ denotes a hydrogen or halogen atom, a C$_1$ to C$_4$ alkyl residue, a C$_1$ to C$_4$ monohydroxyalkyl residue, a C$_2$ to C$_4$ polyhydroxyalkyl residue, a (C$_1$ to C$_4$)alkoxy-(C$_1$ to C$_4$)alkyl residue, a C$_1$ to C$_4$ aminoalkyl residue, or a C$_1$ to C$_4$ cyanoalkyl residue, G$^{15}$ denotes hydrogen, a C$_1$ to C$_4$ alkyl residue, a C$_1$ to C$_4$ monohydroxyalkyl residue, a C$_2$ to C$_4$ polyhydroxyalkyl residue, a phenyl residue, or a benzyl residue, and G$^{16}$ denotes hydrogen or a halogen atom.

The substituents used in formula (E3) are defined herein by analogy with the statements made above.

Exemplary p-aminophenols of formula (E3) include p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy) phenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol, and physiologically acceptable salts thereof.

Exemplary compounds of formula (E3) include p-aminophenol, 4-amino-3-methylphenol, 4-amino-2-aminomethylphenol, 4-amino-2-(α,β-dihydroxyethyl)phenol, and 4-amino-2-(diethylaminomethyl)phenol.

The developer component can furthermore be selected from o-aminophenol and derivatives thereof such as, for example, 2-amino-4-methylphenol, 2-amino-5-methylphenol, or 2-amino-4-chlorophenol.

The developer component can moreover be selected from heterocyclic developer components such as, for example, the pyridine, pyrimidine, pyrazole, pyrazolopyrimidine derivatives and physiologically acceptable salts thereof.

Exemplary pyridine derivatives include the compounds that are described in British patents GB 1 026 978 and GB 1 153 196, such as 2,5-diaminopyridine, 2-(4-methoxyphenyl) amino-3-aminopyridine, 2,3-diamino-6-methoxypyridine, 2-(β-methoxyethyl)amino-3-amino-6-methoxypyridine, and 3,4-diaminopyridine.

Exemplary pyrimidine derivatives include the compounds described in German patent DE 2 359 399, Japanese application JP 02019576 A2, or application WO 96/15765, for example 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, and 2,5,6-triaminopyrimidine.

Exemplary pyrazole derivatives include the compounds described in patents DE 3 843 892, DE 4 133 957, and patent applications WO 94/08969, WO 94/08970, EP 740 931, and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.-butyl-1-methylpyrazole, 4,5-diamino-1-tert.-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, and 3,5-diamino-4-(β-hydroxyethyl)amino-1-methylpyrazole.

Exemplary pyrazolopyrimidine derivatives include the derivatives of pyrazolo[1,5-a]pyrimidine of formula (E4) below and tautomeric forms thereof, provided a tautomeric equilibrium exists:

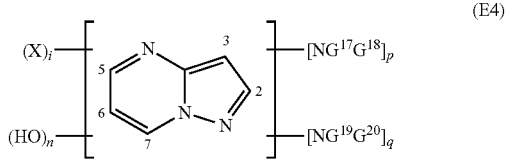

(E4)

where:
G$^{17}$, G$^{18}$, G$^{19}$ and G$^{20}$ denote, mutually independently, a hydrogen atom, a C$_1$ to C$_4$ alkyl residue, an aryl residue, a $C_1$ to $C_4$ hydroxyalkyl residue, a $C_2$ to $C_4$ polyhydroxyalkyl residue, a ($C_1$ to $C_4$)alkoxy-($C_1$ to $C_4$)alkyl residue, a $C_1$ to $C_4$ aminoalkyl residue that optionally can be protected by an acetyl ureide or a sulfonyl residue, a ($C_1$ to $C_4$)alkylamino-($C_1$ to $C_4$)alkyl residue, a di-[($C_1$ to $C_4$)alkyl]-($C_1$ to $C_4$)aminoalkyl residue, the dialkyl residues optionally forming a carbon cycle or a heterocycle having five or six chain members, a $C_1$ to $C_4$ hydroxyalkyl residue, or a di-($C_1$ to $C_4$) [hydroxyalkyl]-($C_1$ to $C_4$)aminoalkyl residue;

the X residues denote, mutually independently, a hydrogen atom, a $C_1$ to $C_4$ alkyl residue, an aryl residue, a $C_1$ to $C_4$ hydroxyalkyl residue, a $C_2$ to $C_4$ polyhydroxyalkyl residue, a $C_1$ to $C_4$ aminoalkyl residue, a ($C_1$ to $C_4$) alkylamino-($C_1$ to $C_4$)alkyl residue, a di-[($C_1$ to $C_4$)alkyl]-($C_1$- to $C_4$) aminoalkyl residue, the dialkyl residues optionally forming a carbon cycle or a heterocycle having five or six chain members, a $C_1$ to $C_4$ hydroxyalkyl residue or a di-($C_1$ to $C_4$ hydroxyalkyl)aminoalkyl residue, an amino residue, a $C_1$ to $C_4$ alkyl- or di-($C_1$ to $C_4$ hydroxyalkyl)amino residue, a halogen atom, a carboxylic acid group, or a sulfonic acid group, i has the value 0, 1, 2, or 3,
p has the value 0 or 1,
q has the value 0 or 1, and
n has the value 0 or 1,
with the provision that
the sum of p+q is not equal to 0,
if p+q is equal to 2, n has the value 0 and the groups $NG^{17}G^{18}$ and $NG^{19}G^{20}$ occupy positions (2,3); (5,6); (6,7); (3,5) or (3,7);
if p+q is equal to 1, n has the value 1 and the groups $NG^{17}G^{18}$ (or $NG^{19}G^{20}$) and the OH group occupy positions (2,3); (5,6); (6,7); (3,5) or (3,7).

The substituents used in formula (E4) are defined by analogy with the statements made above.

If the pyrazolo[1,5-a]pyrimidine of the above formula (E4) contains a hydroxy group at one of positions 2, 5, or 7 of the ring system, a tautomeric equilibrium exists that is depicted, for example, in the following diagram:

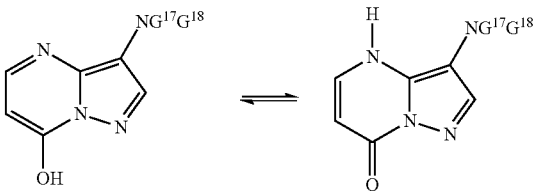

Among the pyrazolo[1,5-a]pyrimidines of the above formula (E4), the following may be mentioned:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
3-amino-7-dimethylamino-2,5-dimethylpyrazolo[1,5-a]pyrimidine;

as well as physiologically acceptable salts thereof and tautomeric forms thereof, if a tautomeric equilibrium exists.

As described in the literature, the pyrazolo[1,5-a]pyrimidines of the above formula (E4) can be produced by cyclization proceeding from an aminopyrazole or from hydrazine.

In a further embodiment, compositions B contain at least one coupler component.

The coupler components generally used include m-phenylenediamine derivatives, naphthols, resorcinol and resorcinol derivatives, pyrazolones, and m-aminophenol derivatives. 1-Naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methylpyrazolone-5,2,4-dichloro-3-aminophenol, 1,3-bis-(2',4'-diaminophenoxy)propane, 2-chlororesorcinol, 4-chlororesorcinol, 2-chloro-6-methyl-3-aminophenol, 2-amino-3-hydroxypyridine, 2-methylresorcinol, 5-methylresorcinol, and 2-methyl-4-chloro-5-aminophenol are particularly suitable as coupler substances.

Exemplary coupler components include:
(A) m-aminophenol and derivatives thereof such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4- chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, and 2,4-dichloro-3-aminophenol,
(B) o-aminophenol and derivatives thereof,
(C) m-diaminobenzene and derivatives thereof such as, for example, 2,4-diaminophenoxyethanol, 1,3-bis-(2',4'-diaminophenoxy)propane, 1-methoxy-2-amino-4-(2'-hydroxyethylamino)benzene, 1,3-bis-(2',4'-diaminophenyl)propane, 2,6-bis-(2'-hydroxyethylamino)-1-methyl benzene, 2-({3-[(2-hydroxyethyl)amino]-4-methoxy-5-methyl phenyl}amino)ethanol, 2-({3-[(2-hydroxyethyl)amino]-2-methoxy-5-methylphenyl}amino)ethanol, 2-[3-morpholin-4-ylphenyl)amino]ethanol, 3-amino-4-(2-methoxyethoxy)-5- methylphenylamine, and 1-amino-3-bis-(2'-hydroxyethyl) aminobenzene,
(D) o-diaminobenzene and derivatives thereof such as, for example, 3,4-diaminobenzoic acid and 2,3-diamino-1-methylbenzene,
(E) di-resp. trihydroxybenzene derivatives such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol, and 1,2,4- trihydroxybenzene,
(F) pyridine derivatives such as, for example, 2,6-dihydroxypyridine, 2-amino-3-hydroxypyridine, 2-amino-5-chloro-3- hydroxypyridine, 3-amino-2-methylamino-6-methoxypyridine, 2,6- dihydroxy-3,4-dimethylpyridine, 2,6-dihydroxy-4-methylpyridine, 2,6-diaminopyridine, 2,3- diamino-6- methoxypyridine and 3,5-diamino-2,6-dimethoxypyridine,
(G) naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene, and 2,3-dihydroxynaphthalene, (H) morpholine derivatives such as, for example, 6-hydroxybenzomorpholine and 6-aminobenzomorpholine,
(I) quinoxaline derivatives such as, for example, 6-methyl-1,2,3,4-tetrahydroquinoxaline,
(J) pyrazole derivatives such as, for example, 1-phenyl-3-methylpyrazol-5-one,
(K) indole derivatives such as, for example, 4-hydroxyindole, 6-hydroxyindole, and 7-hydroxyindole,
(L) pyrimidine derivatives such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or
(M) methylenedioxybenzene derivatives such as, for example, 1-hydroxy-3,4-methylenedioxybenzene, 1-amino-3,4-methylenedioxybenzene, and 1-(2'-hydroxyethyl)amino-3,4-methylenedioxybenzene,
and physiologically acceptable salts thereof.

Particularly suitable coupler components include 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol, and 2,6-dihydroxy-3,4-dimethylpyridine.

In an embodiment, compositions B contain both the developer components and the coupler components in a quantity of from about 0.005 to about 20 wt. %, for example from about 0.1 to about 5 wt. %, based in each case on the total weight of composition B. Developer components and coupler components are, in this context, generally used in approximately molar quantities with respect to one another. Although molar utilization has proven useful, a certain excess of individual oxidation dye precursors is not disadvantageous, so that developer components and coupler components can be contained at a molar ratio of from about 1:0.5 to about 1:3, such as from about 1:1 to about 1:2.

In a further embodiment, compositions B contain as an oxidation dye precursor at least one precursor of a bioanalogous dye. Those indoles and indolines that comprise at least one hydroxy or amino group, preferably as a substituent on the six-membered ring, are suitable for use as precursors of bioanalogous dyes. These groups can carry further substituents, e.g. in the form of an etherification or esterification of the hydroxy group or an alkylation of the amino group. In another embodiment, compositions B contain at least one indole derivative and/or one indoline derivative.

Particularly suitable as precursors of bioanalogous hair dyes are derivatives of 5,6-dihydroxyindoline of formula (IIa):

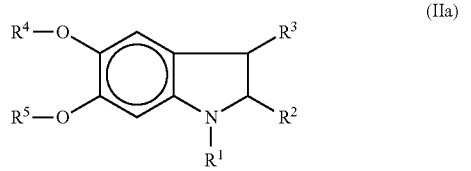

in which, mutually independently:
1. $R^1$ denotes hydrogen, a $C_1$ to $C_4$ alkyl group, or a $C_1$ to $C_4$ hydroxyalkyl group,
2. $R^2$ denotes hydrogen or a —COOH group, where the —COOH group can also be present as a salt with a physiologically acceptable cation,
3. $R^3$ denotes hydrogen or a $C_1$ to $C_4$ alkyl group,
4. $R^4$ denotes hydrogen, a $C_1$ to $C_4$ alkyl group, or a —CO—$R^6$ group in which $R^6$ denotes a $C_1$ to $C_4$ alkyl group, and
5. $R^5$ denotes one of the groups recited under $R^4$,
as well as physiologically acceptable salts of these compounds with an organic or inorganic acid.

Exemplary derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline, and 4-aminoindoline.

Particularly suitable within this group are N-methyl-5,6-dihydroxyindoline, N-ethyl-5,6-dihydroxyindoline, N-propyl-5,6-dihydroxyindoline, N-butyl-5,6-dihydroxyindoline, and in particular 5,6-dihydroxyindoline.

Also particularly suitable as precursors of bioanalogous hair dyes are derivatives of 5,6-dihydroxyindole of formula (IIb):

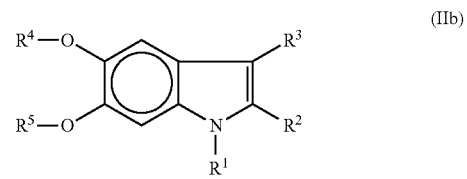

in which, mutually independently:
1. $R^1$ denotes hydrogen, a $C_1$ to $C_4$ alkyl group, or a $C_1$ to $C_4$ hydroxyalkyl group,
2. $R^2$ denotes hydrogen or a —COOH group, where the —COOH group can also be present as a salt with a physiologically acceptable cation,
3. $R^3$ denotes hydrogen or a $C_1$ to $C_4$ alkyl group,
4. $R^4$ denotes hydrogen, a $C_1$ to $C_4$ alkyl group, or a —CO—$R^6$ group in which $R^6$ denotes a $C_1$ to $C_4$ alkyl group, and
5. $R^5$ denotes one of the groups recited under $R^4$,
as well as physiologically acceptable salts of these compounds with an organic or inorganic acid.

Particularly suitable derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole, and 4-aminoindole.

Particularly to be emphasized within this group are N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

The indoline and indole derivatives can be used in compositions B both as free bases and in the form of their physiologically acceptable salts with inorganic or organic acids, e.g. the hydrochlorides, sulfates, and hydrobromides. The indole or indoline derivatives are contained therein usually in quantities of, for example, from about 0.05 to about 10 wt. %, such as from about 0.2 to about 5 wt. %.

In a further embodiment, the indoline or indole derivative is used in compositions B in combination with at least one amino acid or one oligopeptide. The amino acid is for example an α-amino acid, such as arginine, ornithine, lysine, serine, and histidine, in particular arginine.

In another embodiment, composition B contains at least one substantive dye.

In addition to the oxidation dye precursors or alternatively to those coloring agents, compositions B can also contain substantive dyes.

The substantive dyes are, for example, selected from the nitrophenylenediamines, nitroaminophenols, azo dyes, anthraquinones, or indophenols.

Exemplary substantive dyes are the compounds known under the international designations resp. trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-1-hydroxy-4-nitrobenzene.

Compositions B may also contain a cationic substantive dye. Exemplary cationic substantive dyes in this context are 1. cationic triphenylmethane dyes such as, for example, Basic Blue 7, Basic Blue 26, Basic Violet 2, and Basic Violet 14;
2. aromatic systems that are substituted with a quaternary nitrogen group, such as, for example, Basic Yellow 57, Basic Red 76, Basic Blue 99, Basic Brown 16, and Basic Brown 17; and
3. substantive dyes that contain at least one heterocycle which comprises at least one quaternary nitrogen atom, as recited, for example, in Claims 6 to 11 in EP-A2-998 908, to which reference is explicitly made at this juncture.

Exemplary cationic substantive dyes of group (c) are, in particular, the following compounds:

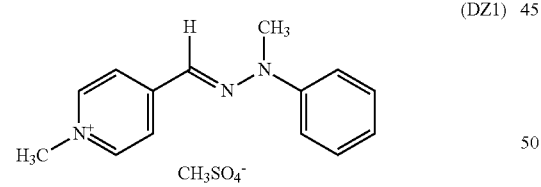

(DZ1)

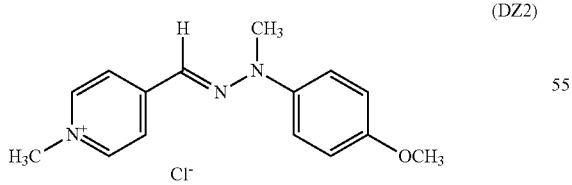

(DZ2)

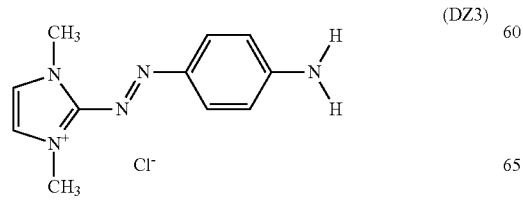

(DZ3)

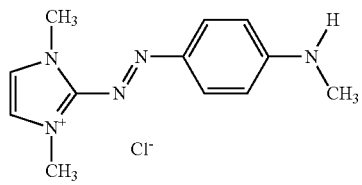

(DZ4)

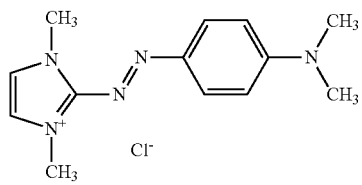

(DZ5)

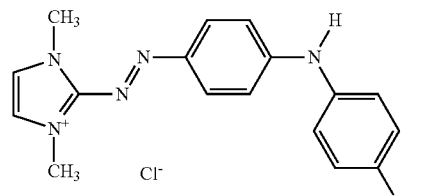

(DZ6)

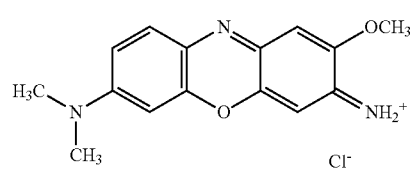

(DZ7)

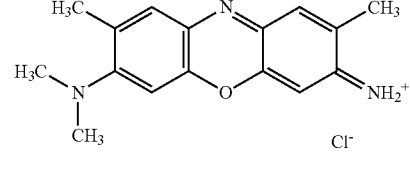

(DZ8)

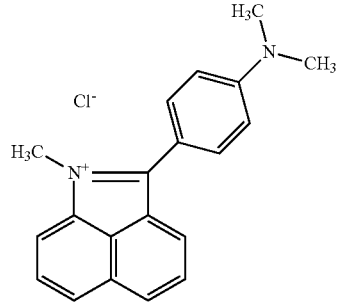

(DZ9)

The compounds of formulas (DZ1), (DZ3), and (DZ5), which are also known under the designations Basic Yellow 87, Basic Orange 31, and Basic Red 51, are suitable cationic substantive dyes of group (c).

The cationic substantive dyes that are marketed under the trademark Arianor® are likewise suitable cationic substantive dyes.

In addition, compositions B can also contain substantive dyes occurring in nature, for example such as those contained in henna red, henna neutral, henna black, chamomile blossom, sandalwood, black tea, buckthorn bark, salvia, logwood, madder root, catechu, Spanish cedar, and alkanna root.

Compositions B contain the substantive dyes, for example, in a quantity from about 0.01 to about 20 wt. %, based on the total utilization preparation in the respective container.

In a further embodiment, a hair-bleaching agent, such as a hair-bleaching powder, is used as composition B. To generate the hair-bleaching effect, these hair-bleaching agents for example contain so-called "boosters." These are as a rule solid peroxo compounds that do not represent addition products of hydrogen peroxide with other components. The selection of these peroxo compounds is not subject, in principle, to any limitations; usual peroxo compounds known to the skilled artisan are, for example, ammonium peroxodisulfate, potassium peroxodisulfate, sodium peroxodisulfate, ammonium persulfate, potassium persulfate, sodium persulfate, potassium peroxodiphosphate, percarbonates such as magnesium percarbonate, and peroxides such as barium peroxide. Among these peroxo compounds, which can also be used in combination, the inorganic compounds are suitable. The peroxodisulfates, in particular ammonium peroxodisulfate, are particularly suitable.

The peroxo compounds are contained in the hair-bleaching agents used herein as composition B in quantities, for example, of from about 2 to about 50 wt. %, such as in quantities of from about 10 to about 35 wt. %. Methods according to exemplary embodiments are characterized in that composition B contains an oxidizing agent, for example, of from about 5.0 to about 50 wt. %, for example, about 10 to about 45 wt. %, for example about 15 to about 40 wt. %, such as about 20 to about 35 wt. % persulfate, based in each case on the total weight of composition B.

As a further component, the hair-bleaching agents contemplated herein contain an alkalizing agent that serves to establish the alkaline pH of the utilization mixture. The usual alkalizing agents likewise known to the skilled artisan for hair-bleaching agents can be used, for example, hydroxides, carbonates, hydrogen carbonates, hydroxycarbonates, silicates, in particular metasilicates of ammonium, alkali metals, and alkaline earth metals, as well as alkali phosphates. In an embodiment, the hair-bleaching agents contemplated herein contain at least two different alkalizing agents. Mixtures of, for example a hydroxycarbonate and a metasilicate are suitable in this context.

The weight proportion of the alkalizing agent in terms of the total weight of the hair-bleaching agent used as composition B is, for example, from about 5 to about 50 wt. %, for example about 10 to about 45 wt. %, such as about 12 to about 40 wt. %.

If a hair-bleaching agent is used as composition B, the agent is present for example in powder form, a component for dedusting the finely powdered formulation usually additionally being added. Such dedusting agents are usually oils, liquid waxes, ether derivatives, but also solvents that are liquid at 25° C., selected from the group of the hydrocarbons, the alcohols, the esters, and the ketones, for example 3-methoxybutanol, benzyl alcohol, 1,2-propanediol, hexanol, cyclohexanone, propylene carbonate, and ethyl diglycol.

Composition B can contain a thickening agent to adjust the viscosity, in which context in particular solid compositions B, in particular solid, bleaching-agent-containing compositions B, contain for example about 0.5 to about 20 wt. %, for example about 1.0 to about 15 wt. %, such as about 1.5 to about 10 wt. % xanthan and/or carboxy cellulose.

The coloring agents manufactured as contemplated herein, that is, compositions A and B used for manufacture, can contain further active substances, adjuvants, and additives such as, for example:

nonionic polymers such as, for example, vinylpyrrolidone/vinyl acrylate copolymers, polyvinylpyrrolidone, vinylpyrrolidone/vinyl acetate copolymers, and polysiloxanes, cationic polymers such as quaternized cellulose ethers, polysiloxanes having quaternary groups, dimethyldiallylammonium chloride polymers, acrylamide/dimethyldiallylammonium chloride copolymers, dimethylaminoethyl methacrylate/vinylpyrrolidone copolymers quaternized with diethyl sulfate, vinylpyrrolidone/imidazolinium methochloride copolymers, and quaternized polyvinyl alcohol, zwitterionic and amphoteric polymers such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers, and acrylic acid/ethyl acrylate/N-tert-butylacrylamide terpolymers, thickening agents such as, for example, agar-agar, guar gum, alginates, xanthan gum, gum arabic, karaya gum, locust bean flour, linseed gums, dextrans, cellulose derivatives, e.g. methyl cellulose, hydroxyalkyl cellulose, and carboxymethyl cellulose, starch fractions and derivatives such as amylose, amylopectin, and dextrins, clays such as e.g. bentonite, or entirely synthetic hydrocolloids such as, for example, polyvinyl alcohol, structuring agents such as maleic acid and lactic acid, hair-conditioning compounds such as phospholipids, for example soy lecithins, egg lecithin, and kephalins, protein hydrolysates, in particular hydrolysates of elastin, collagen, keratin, milk protein, soy protein, and wheat protein, condensation products thereof with fatty acids, and quaternized protein hydrolysates, perfume oils, dimethylisosorbide, and cyclodextrins, solvents and solubilizers such as ethanol, isopropanol, ethylene glycol, propylene glycol, and diethylene glycol, fiber-structure-improving active substances, in particular mono-, di- and oligosaccharides such as, for example, glucose, galactose, fructose, fruit sugars, and lactose, quaternized amines such as methyl-1-alkylamidoethyl-2-alkylimidazolinium methosulfate, defoamers such as silicones, dyes for coloring the agent, anti-dandruff active substances such as zinc omadine and climbazol, light-protection agents, in particular derivatized benzophenones, cinnamic acid derivatives, and triazines, substances for adjusting pH, such as e.g. usual acids, in particular edible acids, and bases, active substances such as allantoin, pyrrolidonecarboxylic acids and salts thereof, as well as bisabolol;

vitamins, provitamins, and vitamin precursors, in particular those of the groups A, $B_3$, $B_5$, $B_6$, C, E, F, and H, plant extracts such as the extracts from green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root, cholesterol, consistency agents such as sugar esters, polyol esters, or polyolalkyl ethers, fats and waxes such as spermaceti, beeswax, Montan wax, and paraffins, fatty acid alkanolamides, complexing agents such as EDTA, NTA, β-alaninediacetic acid, and phosphonic acids, swelling and penetration substances such as glycerol, propylene glycol monoethyl ether, carbonates, hydrogen carbonates, guanidines, ureas, and primary, secondary, and tertiary phosphates, opacifiers such as latex, styrene/PVP and styrene/acrylamide copolymers, luster agents such as ethylene glycol mono- and distearate as well as PEG-3 distearate, preservatives, stabilizing agents for hydrogen peroxide and other oxidizing agents, propellants such as propane/butane mixtures, $N_2O$, dimethyl ether, $CO_2$, and air, antioxidants.

Exemplary methods contemplated herein serve for the manufacture of coloring agents for keratin fibers having a viscosity of from about 10,000 to about 100,000 mPas, for example of from about 30,000 to about 50,000 mPas (Brookfield RVF viscosimeter, spindle #4, 20 rpm, 20° C.).

The coloring agent for keratin fibers that is obtained as an end product of the various embodiments of the method has for example a pH in the range of from about 5 to about 12, such as from about 7.5 to about 11.

As stated initially, the method contemplated herein serves in particular for the manufacture of coloring agents for human hair. Methods according to the various embodiments are therefore characterized in that the coloring agent for keratin fibers is applied onto keratin fibers, such as human hair, after exiting from container B. Discharge of the coloring agent for example occurs in this context immediately, i.e. within a period of less than about 30 minutes, for example less than about 15 minutes, for example less than about 10 minutes, such as less than about 5 minutes.

Exemplary methods for manufacturing a coloring agent for keratin fibers from a first composition A and a second composition B are those in which the first composition A, containing 0 to about 50 wt. %, for example about 0.5 to about 50 wt. % of an oxidizing agent, is directed from a container A by means of a filler apparatus through an inlet opening into a second container B containing the second composition B, where composition B contains about 0.005 to about 20 wt. % of an oxidation dye precursor, wherein composition A is introduced into container B at a pressure above about 1.1 bar, for example above about 2.0 bar, for example above about 5.0 bar, such as in the range of from about 10 to 20, and container B forms, as a result of the introduction of composition A, at least one exit opening out of which the coloring agent for keratin fibers exits from container B as a mixture of compositions A and B.

A further embodiment herein is a container encompassing a container wall closing off the container on the outside, a weakening line integrated into the container wall, a composition, present in the container, encompassing an oxidation dye precursor or a substantive dye.

An additional embodiment is a container encompassing a container wall closing off the container on the outside, a weakening line integrated into the container wall, a static mixer integrated into the container, a composition, present in the container, encompassing an oxidation dye precursor or a substantive dye.

Also an embodiment herein is a container encompassing a container wall closing off the container on the outside, a spike which is suitable for punching through the container wall upon exertion of a force onto the spike and/or onto the container wall, a composition, present in the container, encompassing an oxidation dye precursor or a substantive dye.

Also contemplated herein is a container encompassing a container wall closing off the container on the outside, a spike which is suitable for punching through the container wall upon exertion of a force onto the spike and/or onto the container wall, a static mixer integrated into the container, a composition, present in the container, encompassing an oxidation dye precursor or a substantive dye.

The weight proportion of the oxidation dye precursors in terms of the total weight of the compositions present in the aforesaid containers is, for example, from about 0.005 to about 20 wt. %.

The weight proportion of the substantive dyes in terms of the total weight of the compositions present in the aforesaid containers is, for example, from about 0.01 to about 20 wt. %.

To avoid repetition, reference is made regarding the chemical nature of the oxidation dye precursor, of the substantive dye, and of the other optional ingredients of the container, to the statements above relating to container B.

The volume of the aforesaid containers is, for example, from about 5 to about 100 ml, for example from about 10 to about 80 ml, such as, from about 20 to about 60 ml.

Exemplary containers have a cylindrical lateral surface, a planar upper side, and an underside of planar or conical configuration located opposite the upper side. Particularly suitable containers comprise a flange on which is fastened a sealing film closing off the container. A flange of this kind simplifies, for example, fastening of the container by means of an adhesive, latching, snap-on, or clamping mechanism in the apparatus used to carry out the method contemplated herein.

The aforesaid containers are produced for example from chemically inert materials. The group of those materials includes, for example, aluminum, or plastics such as polypropylene.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. A method for manufacturing a coloring agent for keratin fibers from a first composition A and a second composition B, the method comprising the steps of:

directing the first composition A from a container A by a filler apparatus through an inlet opening into a second container B containing the second composition B, and forming in the container B, as a result of an introduction of the first composition A and/or an action of the filler apparatus, an exit opening out of which the coloring agent for the keratin fibers exits from the container B as a mixture of the first composition A and the second composition B,
wherein the first composition A is introduced into the container B at a pressure above about 1.1 bars.

2. The method according to claim 1, wherein the first composition A is introduced into the container B at the pressure above about 2.0 bars.

3. The method according to claim 2, wherein the first composition A is introduced into the container B at the pressure above about 5.0 bars.

4. The method according to claim 3, wherein the first composition A is introduced into the container B at the pressure in a range of from about 10 to about 20 bar.

5. The method according to claim 1, wherein forming comprises forming the exit opening in the container B comprising a weakening line along which the exit opening is formed as the result of the introduction of the first composition A and/or the action of the filler apparatus.

6. The method according to claim 1, wherein forming comprises forming the exit opening in the container B comprising a membrane that is pressed against a spike causing formation of the exit opening as the result of the introduction of the first composition A and/or the action of the filler apparatus.

7. The method according to claim 1, wherein the container B comprises in its interior a static mixing element and wherein forming comprises mixing the first composition A and the second composition B using the static mixing element.

8. A method for manufacturing a coloring agent for keratin fibers from a first composition A and a second composition B, the method comprising the steps of:
directing the first composition A from a container A by a filler apparatus through an inlet opening into a second container B containing the second composition B, and
forming in the container B, as a result of an introduction of the first composition A and/or an action of the filler apparatus, an exit opening out of which the coloring agent for the keratin fibers exits from the container B as a mixture of the first composition A and the second composition B, wherein directing comprises directing the first composition A comprising an oxidizing agent.

9. The method according to claim 8, wherein directing comprises directing the first composition A comprising the oxidizing agent in an amount of from about 0.5 to about 50 wt. % hydrogen peroxide (calculated as 100% $H_2O_2$), based on a total weight of the first composition A.

10. The method according to claim 9, wherein directing comprises directing the first composition A comprising the oxidizing agent in the amount of from about 1.0 to about 20 wt. % hydrogen peroxide, based on the total weight of the first composition A.

11. The method according to claim 10, wherein directing comprises directing the first composition A comprising the oxidizing agent in the amount of from about 2.5 to about 16 wt. % hydrogen peroxide, based on the total weight of the first composition A.

12. The method according to claim 11, wherein directing comprises directing the first composition A comprising the oxidizing agent in the amount of from about 5.0 to about 14 wt. % hydrogen peroxide, based on the total weight of the first composition A.

13. The method according to claim 1, wherein directing the first composition A from the container A by the filler apparatus through the inlet opening into the second container B containing the second composition B comprises directing the first composition A from the container A by the filler apparatus through the inlet opening into the second container B containing the second composition B comprising an oxidation dye precursor or a substantive dye.

14. The method according to claim 13, wherein directing the first composition A from the container A by the filler apparatus through the inlet opening into the second container B containing the second composition B comprising the oxidation dye precursor comprises directing the first composition A from the container A by the filler apparatus through the inlet opening into the second container B containing the second composition B comprising from about 5.0 to about 50 wt. % persulfate, based on a total weight of the first composition A.

15. The method according to claim 14, wherein directing the first composition A from the container A by the filler apparatus through the inlet opening into the second container B containing the second composition B comprising the oxidation dye precursor comprises directing the first composition A from the container A by the filler apparatus through the inlet opening into the second container B containing the second composition B comprising from about 10 to about 45 wt. % persulfate, based on the total weight of the first composition A.

16. The method according to claim 15, wherein directing the first composition A from the container A by the filler apparatus through the inlet opening into the second container B containing the second composition B comprising the oxidation dye precursor comprises directing the first composition A from the container A by the filler apparatus through the inlet opening into the second container B containing the second composition B comprising from about 20 to about 35 wt. % persulfate, based on the total weight of the first composition A.

17. The method according to claim 1, wherein directing the first composition A from the container A by the filler apparatus through the inlet opening into the second container B containing the second composition B comprises directing the first composition A from the container A by the filler apparatus through the inlet opening into the second container B containing the second composition B with the first composition A and the second composition B used at a volume ratio of from about 10:1 to about 1:1.

18. The method according to claim 17, wherein directing the first composition A from the container A by the filler apparatus through the inlet opening into the second container B containing the second composition B comprises directing the first composition A from the container A by the filler apparatus through the inlet opening into the second container B containing the second composition B with the first composition A and the second composition B used at the volume ratio of from about 6:1 to about 2:1.

19. A method for manufacturing a coloring agent for keratin fibers from a first composition A and a second composition B, the method comprising the steps of:
directing the first composition A from a container A by a filler apparatus through an inlet opening into a second container B containing the second composition B, and
forming in the container B, as a result of an introduction of the first composition A and/or an action of the filler apparatus, an exit opening out of which the coloring agent for the keratin fibers exits from the container B as a mixture of the first composition A and the second composition B, wherein the coloring agent is applied onto the keratin fibers after exiting from the container B.

* * * * *